(12) United States Patent
Shodo

(10) Patent No.: US 7,834,767 B2
(45) Date of Patent: Nov. 16, 2010

(54) VISION REGENERATION ASSISTING DEVICE

(75) Inventor: Kenzo Shodo, Kyoto (JP)

(73) Assignee: Nidek Co., Ltd., Gamagori (JP)

( * ) Notice: Subject to any disclaimer, the term of this patent is extended or adjusted under 35 U.S.C. 154(b) by 733 days.

(21) Appl. No.: 11/712,490

(22) Filed: Mar. 1, 2007

(65) Prior Publication Data

US 2007/0208393 A1    Sep. 6, 2007

(30) Foreign Application Priority Data

Mar. 3, 2006  (JP) ............................. 2006-058561

(51) Int. Cl.
*G08B 23/00* (2006.01)
*A61N 1/08* (2006.01)
(52) U.S. Cl. .................... 340/573.1; 607/53; 607/54
(58) Field of Classification Search ............. 340/573.1, 340/407.1, 500, 515, 693.5, 693.9; 607/53, 607/54, 61, 116, 141; 600/331
See application file for complete search history.

(56) References Cited

U.S. PATENT DOCUMENTS

| | | | |
|---|---|---|---|
| 4,628,933 A * | 12/1986 | Michelson | ............. 607/53 |
| 5,476,494 A | 12/1995 | Edell et al. | |
| 5,935,155 A * | 8/1999 | Humayun et al. | ............. 607/54 |
| 6,847,847 B2 * | 1/2005 | Nisch et al. | ............. 607/54 |
| 7,263,403 B2 * | 8/2007 | Greenberg et al. | ............. 607/54 |
| 7,398,124 B2 * | 7/2008 | Fujikado et al. | ............. 607/54 |
| 7,499,754 B2 * | 3/2009 | Greenberg et al. | ............. 607/54 |
| 2004/0102843 A1 | 5/2004 | Yagi | |
| 2004/0127957 A1 | 7/2004 | Fujikado et al. | |
| 2006/0173259 A1 * | 8/2006 | Flaherty et al. | ............. 600/331 |

FOREIGN PATENT DOCUMENTS

JP    A 2004-57628    2/2004

* cited by examiner

*Primary Examiner*—Van T. Trieu
(74) *Attorney, Agent, or Firm*—Oliff & Berridge, PLC

(57) ABSTRACT

A vision regeneration assisting device for regenerating vision by applying electrical stimulation to cells that form a retina, comprises: a plurality of electrodes: a bendable substrate having a first face on which the electrodes are disposed; and a holding portion provided on a second face of the substrate opposite to the first face, the holding portion holding an installation tool used when the substrate is installed in an eye. In this manner, the substrate having the electrodes disposed thereon can be easily installed in the eye.

6 Claims, 4 Drawing Sheets

VISION REGENERATION ASSISTING DEVICE

BACKGROUND OF THE INVENTION

1. Field of the Invention

The present invention relates to a vision regeneration assisting device for regenerating (reviving) vision.

2. Description of the Related Art

In recent years, a vision regeneration assisting device has been proposed for regenerating (reviving) the vision of a patient by applying from an electrode installed in an eye (an eyeball or an orbit) of the patient who is losing eyesight electrical stimulation to cells that form (constitute) the retina (reference should be made to US 2004/0127957A (Japanese Patent Application Laid-open KOKAI No. 2004-057628, for example). In such a device, at least a portion of a substrate having electrodes disposed thereon is placed inside the retina, or outside the retina (between the retina and the choroid, between the choroid and the sclera, in the sclera, or outside the sclera). Therefore, it is preferable that the substrate be bendable, soft, and thin. However, the softer and the thinner the substrate is, the more difficult it becomes to install (place) the substrate in the eye.

SUMMARY OF THE INVENTION

The invention addresses the technical problem of providing a vision regeneration assisting device that can easily be installed in an eye, the device comprising a substrate having electrodes disposed thereon.

In order to solve the technical problem mentioned above, the present invention is characterized by comprising the following construction.

(1) A vision regeneration assisting device for regenerating vision by applying electrical stimulation to cells that form a retina, the device comprising:

a plurality of electrodes:

a bendable substrate having a first face on which the electrodes are disposed; and a holding portion provided on a second face of the substrate that is opposite to the first face, the holding portion holding an installation tool that is used when the substrate is installed in an eye.

(2) The vision regeneration assisting device corroding to (1), wherein the electrodes are disposed at a distal side of the first face, and the holding portion is provided at a distal side of the second face.

(3) The vision regeneration assisting device according to (1), wherein the holding portion includes a pocket portion of which a distal side is closed, and the installation tool is inserted into the pocket portion through an opening thereof.

(4) The vision regeneration assisting device according to (1), wherein the holding portion includes an engagement portion with which the installation tool becomes engaged when the substrate is moved into the eye, and the engagement portion prevents inward directional movement of the installation tool with respect to the substrate and enables outward directional movement of the installation tool with respect to the substrate.

(5) The vision regeneration assisting device according to (4), wherein the engagement portion includes a pocket portion of which an inward directional side is closed and the installation tool is inserted into the pocket portion through an opening thereof.

(6) The vision regeneration assisting device according to (1), wherein the holding portion includes has flexibility by which, when the substrate is installed, the holding portion is pressurized and flattened by intimate contact of biological tissues with the second face.

PREFERRED EMBODIMENTS OF THE INVENTION

Figure 1:
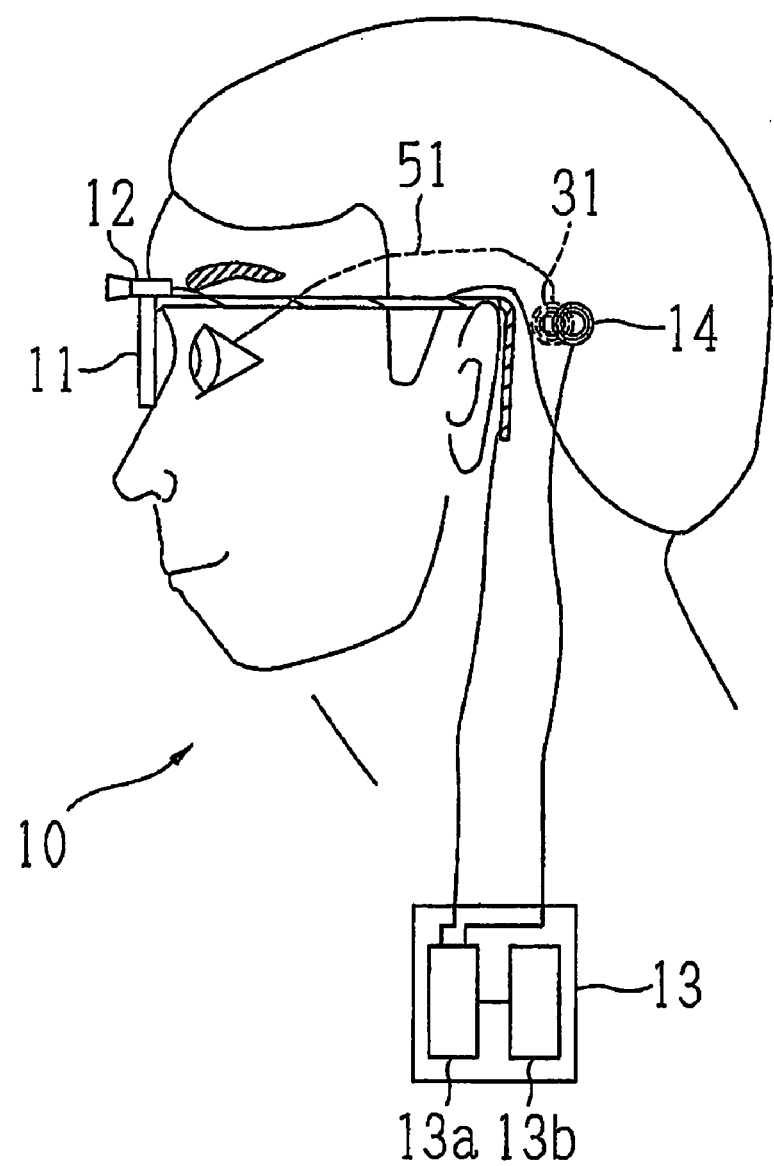
FIG. 1 is a schematic view of an external device of a vision regeneration assisting device according to an embodiment of the present invention.
Figure 2A:
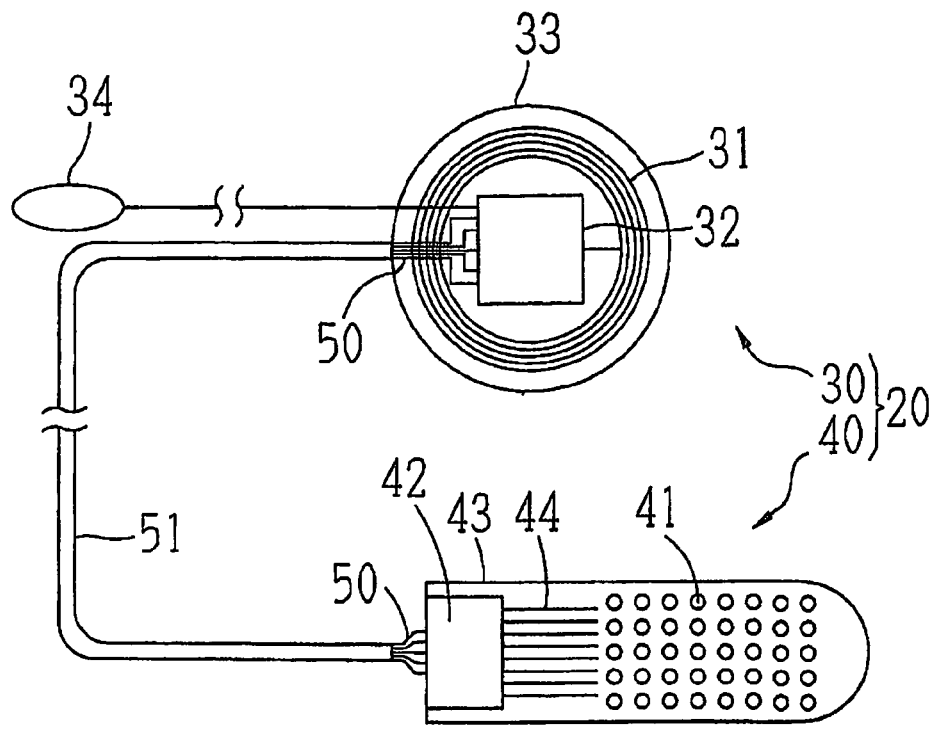
FIG. 2A and FIG. 2B are schematic views of an internal device of the vision regeneration assisting device.
Figure 2B:
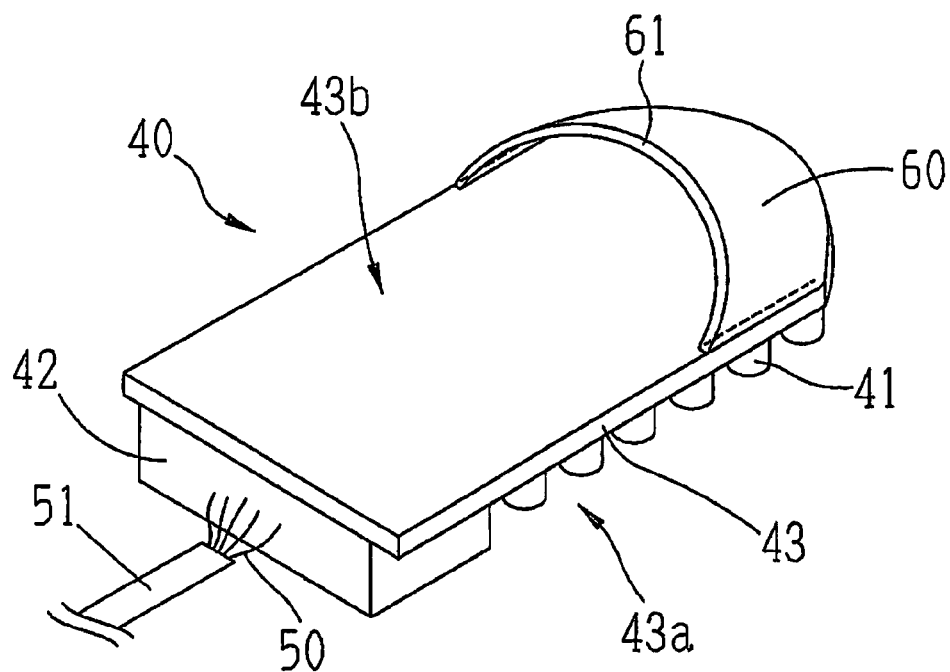
Figure 3A:
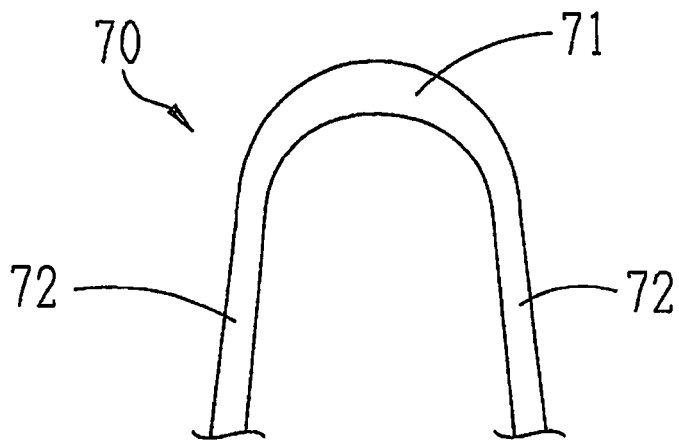
FIG. 3A, FIG. 3B, and FIG. 3C are partial schematic views of an installation tool for installing a stimulation unit of the internal device into an eye.
Figure 3B:
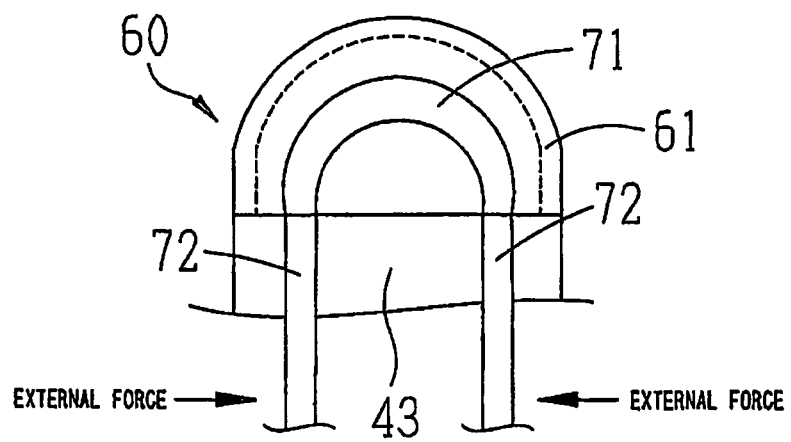
Figure 3C:
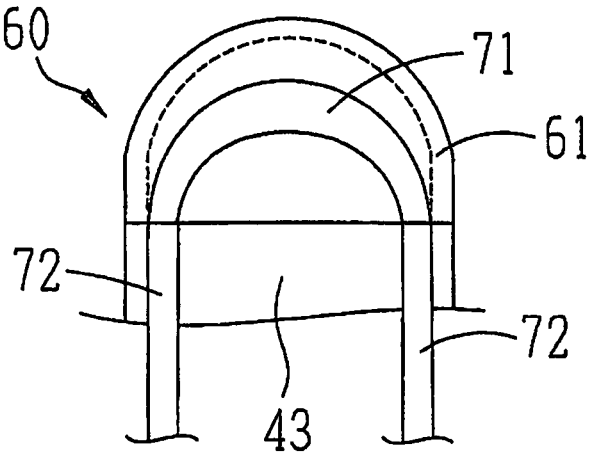
Figure 4:
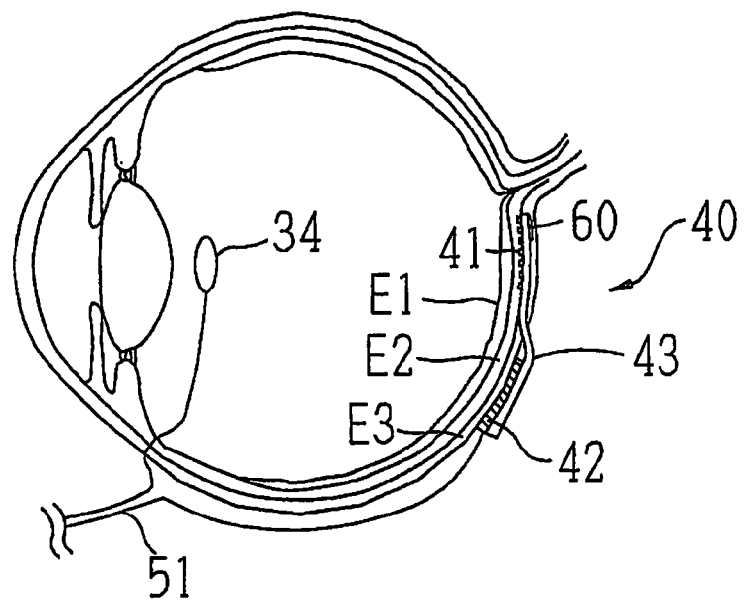
FIG. 4 is a view of a state in which the stimulation unit has been installed in the eye.
Figure 5:
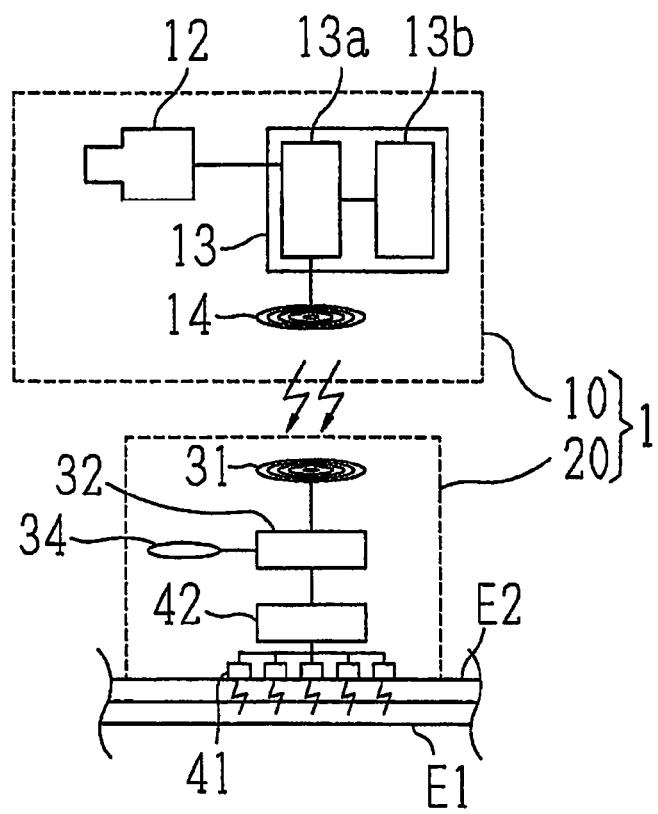
FIG. 5 is a schematic block diagram illustrating a control system for the vision generation assisting device.

An embodiment of the present invention will be described with reference to the accompanying drawings. FIG. 1 is a schematic view of an external device of a vision regeneration assisting device according to an embodiment of the present invention. FIG. 2A and FIG. 2B are schematic views of an internal device of the vision regeneration assisting device. FIG. 3A, FIG. 3B, and FIG. 3C are partial schematic views of an installation tool for installing a stimulation unit of the internal device into an eye. FIG. 4 is a view of a state in which the stimulation unit has been installed in the eye. FIG. 5 is a schematic block diagram illustrating a control system for the vision generation assisting device. The vision regeneration assisting device 1 includes an external device 10 and an internal device 20.

The external device 10 includes a visor 11 that a patent wears; a photography unit 12 made up of equipment such as a CCD camera that is to be mounted on the visor 11; an external unit 13; and a primary coil 14. The visor 11 is formed in the shape of an eyeglass, and is used after being mounted in front of the eyes of a patient. In addition, the photography unit 12 is to be mounted in front of the visor 11, and photographs an object that the patient is to recognize visually.

The external unit 13 includes: a processing unit 13a that has a computation processing circuit such as a CPU; and a power unit (battery) 13b for supply of electric power to the device 1 (the external device 10 and the internal device 20). The processing unit 13a performs image-processing of image data obtained by means of the photography unit 12, and then converts the resulting imaged data into data for electrical stimulation pulse signals.

The primary coil 14 transmits, as electromagnetic waves to the internal device 20, the data for electrical stimulation pulse signals converted by the processing unit 13a and the electric power (power data) from the power unit 13b via the processing unit 13a. A magnet (not shown), used so as to be positionally fixed to a secondary coil 31 that will be described below, is mounted at the center of the primary coil 14.

The internal device 20 includes: a receiver unit 30, which receives the data for electrical stimulation pulse signals and the electric power transmitted from the external device 10; and a stimulation unit 40 for applying electrical stimulation to cells that form the retina.

The receiver unit 30 includes the secondary coil 31, which receives the electromagnetic waves from the external device 10, and a control unit 32. The control unit 32 divides the data for electric stimulation pulse signals, and the electric power received by the secondary coil 31, and converts the data for electrical stimulation pulse signals into the electrical stimulation pulse signals.

The secondary coil 31 and the control unit 32 of the receiver unit 30 are made of metal such as biocompatible metal, and is provided on a substrate 33 that is made of material such as biocompatible resin. A magnet (not shown), used so as to be positionally fixed to the primary coil 14, is mounted at the center of the secondary coil 31.

The stimulation unit 40 includes a plurality of electrodes 41, which output the electrical stimulation pulse signals, and a control unit 42. Each of the electrodes 41 is connected to the control unit 42 through a conductive wire 44. The control unit 42 distributes the electrical stimulation pulse signals into the electrodes 41 on the basis of signals from the control unit 32, and then, causes the electrodes 41 to output the electrical stimulation pulse signals to the cells that form the retina.

The electrodes 41 and the control unit 41 of the stimulation unit 40 are made of material such as biocompatible metal, and are provided on a substrate 43. Because the substrate 43 is to be installed (placed) in the eye, it is preferable that it be formed along the shape of the eyeball, and it is also preferable that, as far as is possible, the burden on the patient be reduced. Therefore, the substrate 43 is made of flexible and biocompatible resin such as polypropylene or polyimide. The thickness of this substrate 43 should be of the order of 50 microns, for example, so that the substrate possesses a predetermined degree of strength and flexibility.

In addition, the receiver unit 30 and the stimulation unit 40 are connected to each other through a plurality of conductive wires 50. The plurality of conductive wires 50 are made of material such as biocompatible metal, and are then tied up into a bundle so as to form in a tube 51 that is made of material such as biocompatible resin.

A pocket portion 60 serving as a holding portion having an opening is provided at the distal side of a second face 43*b* that is positioned opposite to a first face 43*a* of the substrate 43 on which the electrodes 41 and the control unit 42 are disposed. This pocket portion 60 is formed so as to hold therein an installation tool 70, which will be described below. The pocket portion 60 is closed at the distal side and opened at the side opposite to the distal side.

The pocket portion 60 is made of flexible and biocompatible resin such as parylene or polyimide. The thickness of a cover 61 of this pocket portion 60 is of the order of 10 microns, for example, so as to have a predetermined degree of strength and flexibility. In other words, the cover 61 has an extent of flexibility such that, when the stimulation unit 40 (substrate 43) is installed in the eye, the cover 61 can be easily pressurized and flattened by intimate contact with biological tissues. The cover 61 should be thinner than the substrate 43, to a degree such that, even when the cover 61 is pressurized and flattened, there is no drastic change in the thickness of the entire stimulation unit 40 (substrate 43).

As illustrated in FIG. 3A, the installation tool 70 for installing the simulation unit 40 (substrate 43) into the eye has a length such that the stimulation unit 40 (substrate 43) can be installed at a predetermined position within the eye. In addition, the distal end of the installation tool 70 is formed in a substantially U-shape. In a state in which no external force is being applied, a bent distal end part 71 of the installation tool 70 has a width that is slightly less than that of the opening of the pocket portion 60 and that can be inserted; and then, two rod portions 72 extending from the distal end part 71 are formed so as to have a width that gradually increases from the distal end. Then, as illustrated in FIG. 3B, the two rod portions 72 are pressed inwardly, and their widths are reduced, and the installation tool 70 can accordingly be inserted into the pocket portion 60. Then, as illustrated in FIG. 3C, pressing by the rod portions 72 is stopped, and their widths are increased (restored), and the installation tool 70 can be held in the pocket portion 60. In this manner, it is possible to ensure that the installation tool 70 can not be easily moved away from the stimulation unit 40 (substrate 43).

The installation tool 70 may be removed from the pocket portion 60, as shown in FIG. 3B, in the same manner as when it is inserted into the pocket portion 60.

A method for forming the pocket 60 will next be briefly described by way of example. First, a masking material of which a thickness is approximately identical to that of the installation tool 70 is loaded in a predetermined area (preferably, the distal area) of the second face 43*b* of the substrate 43. At this time, the masking material is loaded, with the sole exception of an edge portion that is different to a portion corresponding to the opening in the area. Next, parylene of which a thickness is of the order of 10 microns is fixedly mounted in the area (including the edge portion) over the masking material. Then, the masking material is removed, and the pocket portion 60 is thereby formed.

In addition, a bag having an opening is formed by parylene, and then, the bag is fixedly mounted in a predetermined area (preferably, the distal area) of the second face 43*b* of the substrate 43), and the pocket portion 60 can thereby be formed. In this case, the bag is fixedly mounted so that its closed side is oriented towards the distal side of the substrate 43 (second face 43*b*).

Next, a method for installing the stimulation unit 40 (substrate 43) in the eye will be described. As shown in FIG. 4, a front portion at the distal side of the substrate 43 (a portion at which the electrodes 41 are disposed) is installed between the choroid E2 and the sclera E2 so that the electrodes 41 abuts against the sclera E2. In addition, a rear portion at the rear side of the substrate 43 (a portion at which the control unit 42 is disposed) is installed outside the sclera E3. A part of the sclera E3 is dissected, a sclera pocket is formed, the distal end of the substrate 43 is moved into this sclera pocket and installed, and then, the substrate 43 is fixed, for example, by suture. The installation of the stimulation unit 40 (substrate 43) is thus completed.

The installation tool 70 is used for such installation of the stimulation unit 40 (substrate 43). The installation tool 70 is inserted into the pocket 60, and then, together with the installation tool 70, the stimulation unit 40 (substrate 43) is moved into the sclera pocket. Then, the stimulation unit 40 (substrate 43) is installed at a predetermined position, and the installation tool 70 is then removed from the pocket portion 60.

While in the present embodiment a construction has been described such that the front portion of the stimulation unit 40 at which the electrodes 41 are disposed is installed between the choroid E2 and the sclera E3, the present invention is not limited thereto. A construction may be provided such that the front portion of the stimulation unit 40 is installed at a position at which electrical stimulation can preferably be applied to the cells that form the retina E1. For example, a construction may be provided such that the front portion of the stimulation unit 40 is installed inside the retina E1, between the retina E1 and the choroid E2, in the sclera R3, or outside the sclera E3.

An indifferent electrode 34, as shown in FIG. 4, is installed at a position close to the anterior segment of the eye (in the vitreous body). In this manner, the retina E1 is positioned between the electrodes 41 and the indifferent electrode 34, and, the electrical stimulation pulse signals from the electrodes 41 can then effectively pass through the retina E1.

The secondary coil 31 is installed at a predetermined position in the body in such a way that the signal (the data for electrical stimulation pulse signals and the electric power) from the primary coil 14 can be received. For example, as illustrated in FIG. 1, the receiver unit 30, including the secondary coil 21, is installed under the skin of the temporal part of the patient, and, the primary coil 14 is then placed at a position opposite to the secondary coil 31 on the skin. The magnets are mounted on the primary coil 14 and the secondary coil 31, so that the primary coil 14 is magnetically mounted on the secondary coil 31, and then, the primary coil 14 is retained on the skin of the temporal part.

The tube 51 extends from the control unit 32 of the receiver unit 30 to the eye under the skin of the temporal part, and, is then inserted into the orbit through the inside of the upper eyelid. The tube 51, which has been inserted into the orbit, as illustrated in FIG. 4, is connected to the control unit 42 of the stimulation unit 40 through the outside of the sclera E3.

The holding portion of the installation tool is not limited to the pocket portion 60 described above, as long as it includes an engagement portion with which the installation tool can be engaged when the substrate 43 is moved into the eye by the installation tool, and it thus becomes impossible to move the installation tool in an inward direction (importing direction) relative to the substrate 43 but still possible to move the installation tool in an outward direction relative to the substrate 43. The engagement portion may, for example, be a protrusive portion provided at a predetermined position (preferably, a distal position) of the second face 43b of the substrate 43. The protrusive portion may, for example, have a height of the order of 20 microns to 100 microns to a level such that the installation tool cannot be moved, and such that no adverse influence accordingly occurs after the installation. In addition, a band portion, like the pocket portion 60, may, for example, have a thickness of the order of 10 microns to an extent such that at a time of the installation it is pressurized and flattened by intimate contact of biological tissues with the substrate 43 (second face 43b). The protrusive portion and the band portion may be formed integrally with the substrate 43; may be formed separately from the substrate 43 by use of biocompatible material, or may be fixedly mounted on the substrate 43.

Additional advantages and modifications will readily occur to those skilled in the art. Therefore, the invention in its broader aspect is not limited to the specific details and representative embodiments shown and described herein. Accordingly, various modifications may be made without departing from the spirit or scope of the general inventive concept as defined by the appended claims and their equivalents.

What is claimed is:

1. A vision regeneration assisting device for regenerating vision by applying electrical stimulation to cells that form a retina, the device comprising:
    a plurality of electrodes;
    a bendable substrate having a first face on which the electrodes are disposed; and
    a holding portion provided on a second face of the substrate that is opposite to the first face, the holding portion detachably holding an installation tool that is handled by an operator and used when the substrate is installed in an eye.

2. The vision regeneration assisting device according to claim 1, wherein the electrodes are disposed at a distal side of the first face, and the holding portion is provided at a distal side of the second face.

3. The vision regeneration assisting device according to claim 1, wherein the holding portion includes a pocket portion of which a distal side is closed, and the installation tool is inserted into the pocket portion through an opening thereof.

4. The vision regeneration assisting device according to claim 1, wherein the holding portion includes an engagement portion with which the installation tool becomes engaged when the substrate is moved into the eye, and the engagement portion prevents inward directional movement of the installation tool with respect to the substrate and enables outward directional movement of the installation tool with respect to the substrate.

5. The vision regeneration assisting device according to claim 4, wherein the engagement portion includes a pocket portion of which an inward directional side is closed, and the installation tool is inserted into the pocket portion through an opening thereof.

6. The vision regeneration assisting device according to claim 1, wherein the holding portion is flexible, such that when the substrate is installed, the holding portion is pressurized and flattened by intimate contact of biological tissues with the second face.

* * * * *